United States Patent

Gross et al.

Patent Number: 5,925,030
Date of Patent: Jul. 20, 1999

[54] ORALLY ADMINISTRABLE DELIVERY DEVICE

[75] Inventors: Joseph Gross; John Gerard Kelly, both of Dublin, Ireland

[73] Assignee: Elan Corporation, plc, Dublin, Ireland

[21] Appl. No.: 08/793,497

[22] PCT Filed: Aug. 4, 1995

[86] PCT No.: PCT/IE95/00039

§ 371 Date: Sep. 29, 1997

§ 102(e) Date: Sep. 29, 1997

[87] PCT Pub. No.: WO96/04953

PCT Pub. Date: Feb. 22, 1996

[30] Foreign Application Priority Data

Aug. 15, 1994 [IE] Ireland ..................................... 940643

[51] Int. Cl.⁶ .............................. A61K 9/22; A61M 37/00
[52] U.S. Cl. ................... 604/890.1; 604/141; 604/891.1
[58] Field of Search ............................. 604/890.1, 891.1, 604/19, 20, 133, 140, 141; 607/115, 116, 133; 424/438, 439, 422–426

[56] References Cited

U.S. PATENT DOCUMENTS

| | | | |
|---|---|---|---|
| 3,894,538 | 7/1975 | Richter | 128/260 |
| 3,996,126 | 12/1976 | Rasmussen | 204/271 |
| 4,036,228 | 7/1977 | Theeuwess | 128/260 |
| 4,203,439 | 5/1980 | Theeuwes | 128/260 |
| 4,203,441 | 5/1980 | Theeuwess | 128/260 |
| 4,327,725 | 5/1982 | Cortese et al. | 128/260 |
| 4,331,728 | 5/1982 | Theeuwes | 428/215 |
| 4,344,929 | 8/1982 | Bonsen et al. | 424/15 |
| 4,675,174 | 6/1987 | Eckenhoff | 424/15 |
| 4,765,989 | 8/1988 | Wong et al. | 424/15 |
| 4,783,337 | 11/1988 | Wong et al. | 424/468 |
| 4,786,500 | 11/1988 | Wong | 424/422 |
| 4,955,881 | 9/1990 | Eckenhoff | 604/890 |
| 5,023,076 | 6/1991 | Ayer et al. | 424/78 |
| 5,135,499 | 8/1992 | Tafani et al. | 604/141 |
| 5,318,557 | 6/1994 | Gross | 604/891 |
| 5,354,264 | 10/1994 | Bae et al. | 604/21 |
| 5,358,721 | 10/1994 | Guittard et al. | 424/473 |

FOREIGN PATENT DOCUMENTS

| | | | |
|---|---|---|---|
| 2195461 | 3/1974 | France | A61M 37/00 |
| WO 91/00753 | 1/1991 | WIPO | A61M 31/00 |
| WO 94/01165 | 1/1994 | WIPO | A61M 31/00 |

*Primary Examiner*—Wynn Wood Coggins
*Assistant Examiner*—Patricia M. Bianco
*Attorney, Agent, or Firm*—Kathleen L. Maher

[57] ABSTRACT

Oral drug delivery device having a housing with walls of water permeable material and having at least two chambers separated by a displaceable membrane. The first chamber receives drug and has an orifice through which the drug is expelled under pressure. The second chamber contains at least one of two spaced apart electrodes forming part of an electric circuit which is closed by the ingress of an aqueous ionic solution into the second chamber. When current flows through the circuit, gas is generated and acts on the displaceable membrane to compress the first chamber and expel the active ingredient through the orifice for progressive delivery to the gastrointestinal tract.

12 Claims, 2 Drawing Sheets

ORALLY ADMINISTRABLE DELIVERY DEVICE

FIELD OF THE INVENTION

This invention relates to an orally administrable delivery device which is especially suited for the delivery of an active ingredient such as a drug to the gastrointestinal tract.

BACKGROUND ART

Various types of devices are known for the delivery of active ingredients in a controlled manner to the gastrointestinal tract for absorption into the systemic circulation so as to maximise the efficacy of such active ingredients.

Our International Publication WO 94/01165 describes and claims a medication administering device which comprises a housing of a size enabling it to be introduced into a body cavity. The housing, which is of a material insoluble in body cavity fluids, but which is provided with an opening, is divided into first and second expansible and contractible chambers by a displaceable member. The second chamber includes electrically-controlled means for generating a gas to expand said chamber and force medication contained in the first chamber out through the opening into the body cavity and thus is based on electrolytic technology. The device of our International Publication WO 94/01165 is an example of what is referred to as a "smart" pill.

A "smart" pill is described briefly in Popular Science, May 1992, at page 25. The "smart" pill in question is in the form of a capsule containing a tiny radio transmitter that transmits a continuous signal as it passes through the body so as to enable its location in the body to be detected at any given time. When it reaches a predetermined location, a computer signals the pill to release the medication contained therein by actuating a piston within the capsule to force out medication contained within a chamber in the capsule.

The device of our International Publication WO 94/01165 includes, in certain embodiments, an electrolytic cell and a small battery with associated electronics. In other embodiments, however, the power source is derived from two fine wires of diverse metals wrapped around the exterior surface of the housing. The two wires, in combination with the gastric fluids in which they are immersed and by which they are separated, act as a voltaic cell which is used as the power source for an electrolytic cell within the second chamber.

Thus, although the requirement for a battery is obviated, there are certain drawbacks associated with this method of generating a gas within the second chamber.

Firstly, it is not always possible to achieve the desired rates of gas generation, since the rate of gas generation is directly dependent upon the current passing through the electrolytic cell. This current depends in turn, upon the resistance provided by the electrolytic cell and the magnitude of voltage generated by the voltaic cell on the external surface of the housing. The voltage generated is not always sufficient to drive the electrolytic cell at the desired rate.

Secondly, it is undesirable to use the gastric fluids as the electrolyte for a battery, since the chemical reactions occurring at the electrodes may lead to undesirable products (such as metallic compounds or gases) being created within and released into the gastrointestinal tract.

Thus, it is an object of the present invention to overcome the problems indicated above and to provide a device which is structurally more simple, which is cheaper and easier to manufacture, and which is more compact and more efficient than the devices of the prior art.

DISCLOSURE OF INVENTION

The invention provides such a device which is an orally administrable delivery device comprising a housing with walls of a water permeable material and having at least two chambers: a first chamber adapted to receive an active ingredient and which is provided with an orifice through which the active ingredient is expelled under pressure in a liquid form; and a second chamber containing at least one of two spaced-apart electrodes which form part of an electric circuit which is closed by ingress of an aqueous ionic solution into said second chamber, such that a potential difference is set up between the electrodes and a current flows through said circuit resulting in the generation of a gas at said at least one electrode, and the gas once generated acting on a displaceable membrane to compress the first chamber and expel the active ingredient through the orifice for progressive delivery to the gastrointestinal tract.

The water-permeable material of which the walls are made allow water to enter the chamber substantially immediately, remaining intact throughout the delivery of the active ingredient. Thus, the rate of delivery depends on the electric circuit which generates the gas and not on the rate at which water is permitted to enter the housing. Suitable water-permeable materials are also referred to as hydrophilic materials.

The device according to the invention in its simplest form achieves release of active ingredient to the gastrointestinal tract in a controlled manner similar to that achieved with controlled release multi-particulate formulations and other controlled release oral dosage forms.

The active ingredient which is expelled from the device in a liquid form is immediately available for absorption by the gastrointestinal tract with the attendant advantages, if required. However, the device according to the invention by appropriate selection of the materials of the device and the construction thereof can also be used to achieve delivery of an active ingredient so as to achieve a therapeutic effect over a 24 hour period, if required.

The second chamber preferably contains a pair of spaced-apart electrodes.

However one electrode may be situated outside the housing with the current flowing by ionic transport through the aqueous solution connecting the electrodes through the walls of the housing.

Preferably, the electrodes represent an anode and a cathode, the sum of the half-cell reactions of which is positive and wherein at least one of the electrode reactions produces a gas when said electric circuit is closed.

The anode and cathode can each be in the form of a rod, a sheet, a deposited layer or a compressed powder.

The anode and the cathode will be made from biocompatible materials such as platinum, nickel and silver. For example, one can use a nickel metal anode and a silver chloride cathode. At the nickel cathode, water is converted to oxygen gas and at the silver chloride cathode, the silver chloride is converted to silver metal and chloride ions.

Preferably, the electrodes are connected by a connection which is isolated from the electrolyte. Thus, the electric circuit follows a path from the anode, through the electrolyte to the cathode, and back to the anode via a connection which is isolated from the electrolyte.

Further preferably, the connection is external of the second chamber.

Suitably, the electric circuit includes a micro-processor for controlling the generation of gas. The rate of gas generation depends directly on the magnitude of the current passing through the electrolyte. Thus, by controlling the current, the micro-processor controls the generation of gas.

The rate and amount of gas generation is a function which is controlled by the electric circuit, such as by varying the current over time or by breaking the circuit, and thus stopping the generation of gas, for certain periods of time.

It will be appreciated that a range of fully controllable devices can be provided by constructing them with different electronic units.

Once the device is swallowed, the water permeable housing begins to absorb liquid from the gastrointestinal tract and liquid enters both the first and second chambers. Gas generation commences and simultaneously provides the power necessary to power the electrolytic reaction.

Furthermore, the electric circuit can include a sensor for sensing a condition in the body and can control the generation of gas in response to the output of said sensor.

For example, the sensor may be or include any one or more of the following: a pH sensor, to effect the delivery of the active ingredient to a predetermined region of the gastrointestinal tract; a temperature sensor to control the delivery of the active ingredient in response to body temperature; or a sound sensor, such as a microphone, to control the delivery of the active ingredient in response to the pulse rate.

Such biosensors can provide a feedback to the electric circuit.

In an alternative embodiment the device is equipped with a radio receiver which communicates with the electric circuit such that delivery of the active ingredient can be controlled by providing radio signals from outside the body. A transmitter can also be provided to transmit information relating to the operation of the device or its location in the gastrointestinal tract for example.

The displaceable membrane is preferably made of a flexible material such as polyvinyl chloride or a silicone rubber.

The electrode(s) can be coated on a surface of the second chamber.

The coating of the electrode(s) can be effected by employing such techniques as sputtering, evaporation, the use of compressed powders, printing and the like.

The material of the walls of the device is suitably a non-toxic material which is selected from natural and synthetic materials.

Such materials include plastics materials, cellulose or cellulose derivatives, including paper, or a biodegradable material such as starch. Generally such materials are gas permeable when dry, but gas impermeable when absorbing liquid through the pores or channels in the structure thereof, since the liquid effectively "blocks" the pores.

In the case of the embodiments referred to above, the gas is produced at an accurate rate without the need for a conventional battery.

It will be appreciated that the device in accordance with the invention has substantial advantages when compared with existing micro-encapsulated pills or the so-called "osmotic" pill, primarily in that the "osmotic" pill has a delivery rate which cannot be controlled, but which is predetermined by the structure of the pill. In certain embodiments of the present invention, however, the delivery of the drug can be controlled as precisely as available electronics will allow, and in response to virtually any chosen conditions.

Accordingly, the underlying principle in the case of the device according to the invention is that the electrochemical cell produces gas via spontaneous reactions without the need for an external power source. In essence, the second chamber behaves like a battery; in this case, the product of the reaction is a gas. In order for the cell in the second chamber to operate effectively, the anode and cathode materials must be chosen so that the individual reactions at the anode and cathode together result in a total cell reaction which is spontaneous. The total cell reaction is the sum of the individual anode and cathode reactions. Each reaction is characterised by its half-cell potential which is a known thermodynamic quantity. The half-cell potentials of many reactions are listed in standard reference books. In order for the total cell reaction to be positive (spontaneous), the sum of the anode and cathode half-cell reactions must be positive.

Representative examples of different types of cells which may be accommodated in the second chamber are as follows:

OXYGEN GENERATING CELLS

Anode material: Nickel, platinum, carbon or graphite.

Anode form: Rods, sheets or deposited layers.

Anode reaction to produce oxygen:

| | Half-Cell Potential |
|---|---|
| $2H_2O \rightarrow O_2 + 4H^+ + 4e^-$ | −1.229 |

In order for the total cell reaction to be spontaneous the cathode half-cell reaction must have a positive value greater than +1.229.

Examples are:

| | Half-Cell Potential |
|---|---|
| $Bi_2O_4 + 4H^+ + 2e^- \rightarrow 2BiO + 2H_2O$ | 1.59 |
| $NiO_2 + 4H^+ + 2e^- \rightarrow Ni^{+2} + 2H_2O$ | 1.68 |
| $PbO_2 + 4H^+ + 2e^- \rightarrow Pb^{+2} + 2H_2O$ | 1.455 |

The above cathodes are suitably in the form of deposited layers or compressed powders.

HYDROGEN GENERATING CELLS

Cathode material: Nickel, platinum, carbon or graphite.

Cathode form: Rods, sheets, or deposited layers.

Cathode reaction to produce hydrogen gas:

| | Half-Cell Potential |
|---|---|
| $2H^+ + 2e^- \rightarrow H_2$ | 0.0 |

In order for the total cell reaction to be spontaneous the anode half-cell reaction must have a positive half-cell potential greater than 0.

Examples are:

| | Half-Cell Potential |
|---|---|
| $Al \rightarrow Al^+ + 3e^-$ | +1.66 |
| $Ba \rightarrow Ba^{+2} + 2e^-$ | +2.90 |
| $B + 3H_2O \rightarrow H_3BO_3 + 3H^+ + 3e^-$ | +0.87 |
| $Cr \rightarrow Cr^{+3} + 3e^-$ | +0.74 |
| $Fe \rightarrow Fe^{+2} + 2e^-$ | +0.49 |
| $In \rightarrow In^{+3} + 3e^-$ | +.342 |
| $Ni \rightarrow Ni^{+2} + 2e^-$ | +.250 |
| $Pb \rightarrow Pb^{+2} + 2e^-$ | +.126 |
| $Sn \rightarrow Sn^{+2} + 2e^-$ | +.150 |
| $2Ta + 5H_2O \rightarrow Ta_2O_5 + 10H^+ + 10e^-$ | +0.81 |
| $Ti \rightarrow Ti^{+2} + 2e^-$ | +1.63 |
| $Ti + H_2O \rightarrow TiO^{+2} + 2H^+ + 4e^-$ | +0.89 |

The above anodes are suitably in the form of rods, sheets, or deposited layers.

Similar reactions can occur at basic pH levels. For instance, to produce oxygen at the anode

| | Half-Cell Potential |
|---|---|
| $4OH^- \rightarrow O_2 + 2H_2O + 4e^-$ | −.401 | at a platinum, nickel, carbon or graphite electrode. The corresponding cathode reactions can be chosen from:

| | Half-Cell Potential |
|---|---|
| $2AgO + 2OH^- \rightarrow Ag_2O_3 + H_2O + 2e^-$ | +.74 |
| $MnO_2 + 4OH^- \rightarrow MnO_4^{-2} + 2H_2O + 2e^-$ | +.60 |

The above cathodes are suitably in the form of rods or compressed powders of silver oxide or manganese dioxide.

The orifice is suitably of the order of 0.1 mm or less and is suitably achieved by laser drilling.

The gas once generated cannot escape from the second chamber. It will be appreciated that such gas will be at a relatively low pressure and that the capillary forces generated by the ingress of water will be greater than the pressure of the gas generated, so that the gas will be confined to the second chamber and will cause the displaceable membrane to be displaced, thereby contracting the first chamber and expelling the active ingredient through the orifice.

It will be appreciated also that the orifice provides the path of least resistance for the liquid containing the active ingredient, which will exit the first chamber through the orifice.

The orifice can be initially closed by a material which is soluble in the liquid environment of the gastrointestinal tract.

Accordingly, the material can be gelatinous material or other material used in capsules which is soluble in body fluids.

The gas generation rate builds up slowly, for example for a period of approximately 10 minutes, and thereafter reaches a steady state, unless the electric circuit is adapted to vary the current flowing therethrough.

The device according to the invention will preferably be the size of a regular pill or capsule.

The active ingredient is preferably solid, more particularly a solid in powder form. However, depending on the shelf-life of the active ingredient in liquid form, it is also possible for the active ingredient to already be in a liquid or a semi-solid form in the first chamber at the time of administration of the device.

Suitable active ingredients for administration using the device according to the invention are: peptides, proteins, hormones, including peptide and protein hormones, prostaglandins, analgesics, anti-migraine agents, sedatives, narcotic antagonists, anti-coagulants, anti-emetic agents, anti-infective agents, anti-diabetic agents, cardiovascular agents, anti-hypertensive agents, chelating agents, anti-anginal agents, anti-duretic agents, chemotherapeutic agents and anti-neoplastics.

BRIEF DESCRIPTION OF DRAWINGS

The device will be further illustrated by the following description of an embodiment thereof, given by way of example only with reference to the accompanying Drawings in which.

MODES FOR CARRYING OUT THE INVENTION

Figure 1:
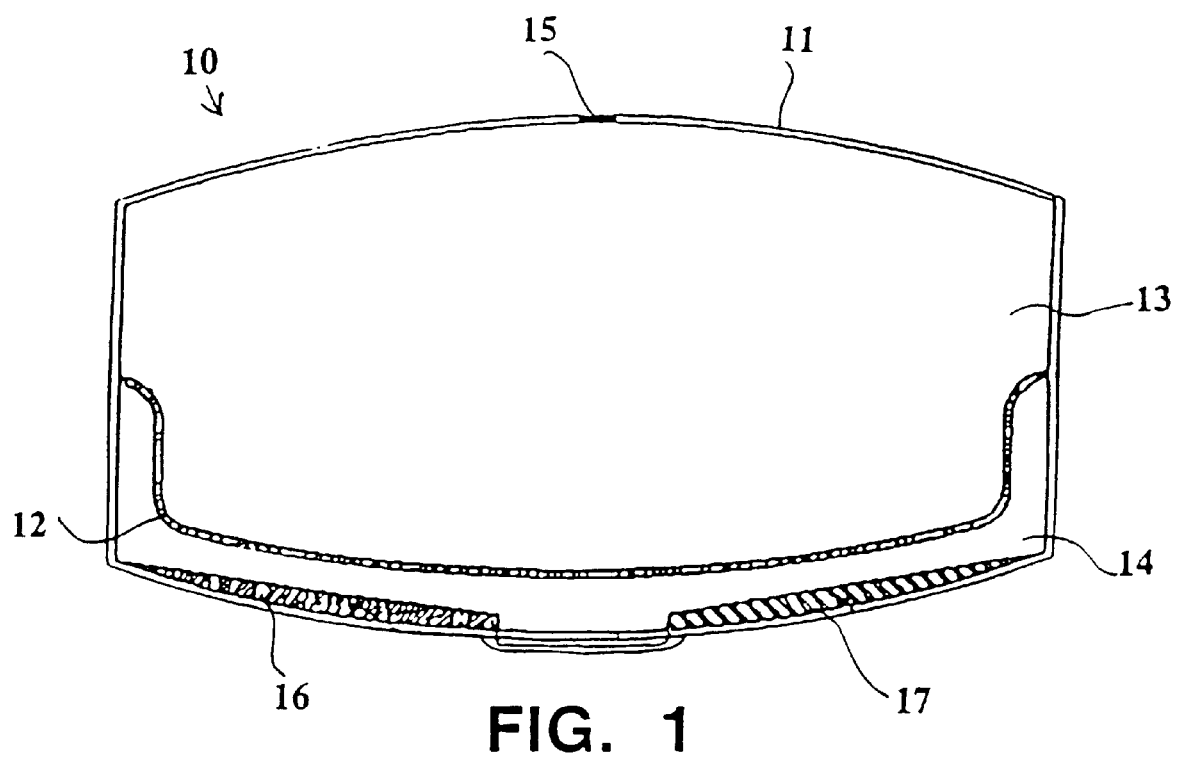
FIG. 1 is a cross section of an embodiment of a device according to the invention.

In FIG. 1, there is illustrated, generally at 10, an orally administrable delivery device according to the invention. The device 10 has a housing 11, the walls of which are formed from starch which is water permeable due to its inherent porosity and through which water and entrained solutes are drawn by capillary action. A membrane 12 within housing 11 defines, on one side thereof, a drug delivery chamber 13 and, on the other side thereof, a gas generation chamber 14. The generation of a gas within gas generation chamber 14 as hereinafter described increases the pressure therein and tends to push membrane 12, which is freely displaceable, upwards so as to reduce the volume of drug delivery chamber 13. The housing 11 is provided with an orifice 15 though which a drug-containing liquid is expelled when drug delivery chamber 13 is contracted. Although gas generation chamber 14 is initially air filled, the capillary pressure tending to draw the liquid into the gas generation chamber 14 is stronger than the resistive gas pressure which tends to oppose the entry of solution into the chamber 14.

When the device 10 is swallowed, liquid from the aqueous environment of the gastrointestinal tract permeates through the hydrophilic starch walls of housing 11 due to the capillary pressure related to the hydrophilic material used. Admission of water into drug delivery chamber 13 causes the drug contained therein (not shown) to be dissolved or suspended in the gastrointestinal fluid, as the case may be.

The drug delivery chamber 13 is initially filled with the drug to be delivered in the form of a powder. Since the walls of the drug delivery chamber 13 are made of hydrophilic material, liquid is admitted into the drug delivery chamber 13 in the same manner as it is admitted into the gas generation chamber 14. If the drug is soluble in water, then the drug is dissolved when the liquid enters the drug delivery chamber 13.

If the drug is water insoluble, a fine powder of the drug will nevertheless form a suspension in the liquid. Thus, the same principles apply as previously described, and the expansion of the gas generation chamber 14 results in the contraction of the drug delivery chamber 13 and the expulsion of the drug-containing liquid (this time in the form of a suspension) from the device 10 to the gastrointestinal tract.

The gas generation chamber 14 contains two electrodes 16,17. Electrode 16 is a nickel metal element and electrode 17 is a silver chloride element.

Figure 2:
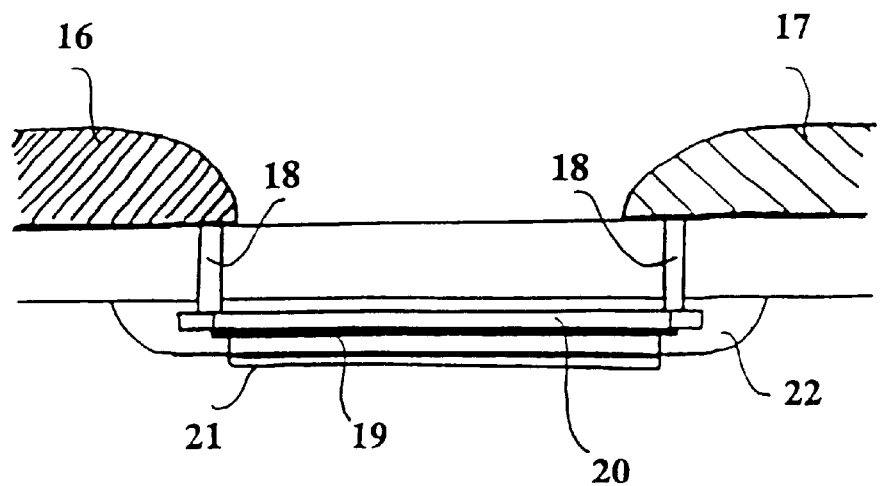
FIG. 2 is an enlarged view of a detail taken from FIG. 1.

Referring additionally to FIG. 2, wherein there is shown a detail of the device of FIG. 1 in an enlarged view, it can be seen that electrodes 16 and 17 are physically isolated from one another but are electrically connected to one another via electrical conductors 18 and a printed circuit 19. The printed circuit 19 is produced as a metallization pattern on an insulating substrate 20.

When an ionic solution bridges the gap between the electrodes 16,17, a circuit is completed. The circuit comprises the electrodes 16,17, the electrical conductors 18, the printed circuit 19 and the ionic solution within chamber 14. When the circuit is completed, a potential difference is set up as a result of the differing half-cell potentials of the two electrodes in solution. This difference in potential leads to the flow of a current through the circuit which results in an electrochemical reaction occurring at the nickel and silver chloride electrodes which are immersed in the solution and connected electrically. At the nickel anode, water is converted to oxygen gas, and at the silver chloride cathode, the silver chloride is converted to silver metal and chloride ions. The reaction of the electrodes with the electrolyte results in gas being generated at the nickel electrode.

Since the printed circuit 19 forms part of the electric circuit, it can be used to control the current flowing through the circuit, and thereby control the rate of generation of gas within gas generation chamber 14. In the embodiment illustrated a pH sensor 21 acts as an input to circuit 19. An insulating plastics layer 22 separates the printed circuit 19 from the external environment, so that the circuit 19 is electrically isolated therefrom, but the pH sensor 21 is immersed in the gastrointestinal fluid surrounding the device 10.

At very low pH levels, gas generation is inhibited by printed circuit 19. In higher pH environments, printed circuit 19 allows the current to flow more freely. Thus, the device illustrated is designed to withhold drug delivery within the stomach (a very low pH environment), and to increase delivery as the device moves into a higher pH environment when it leaves the stomach and enters the duodenum.

Figure 3:
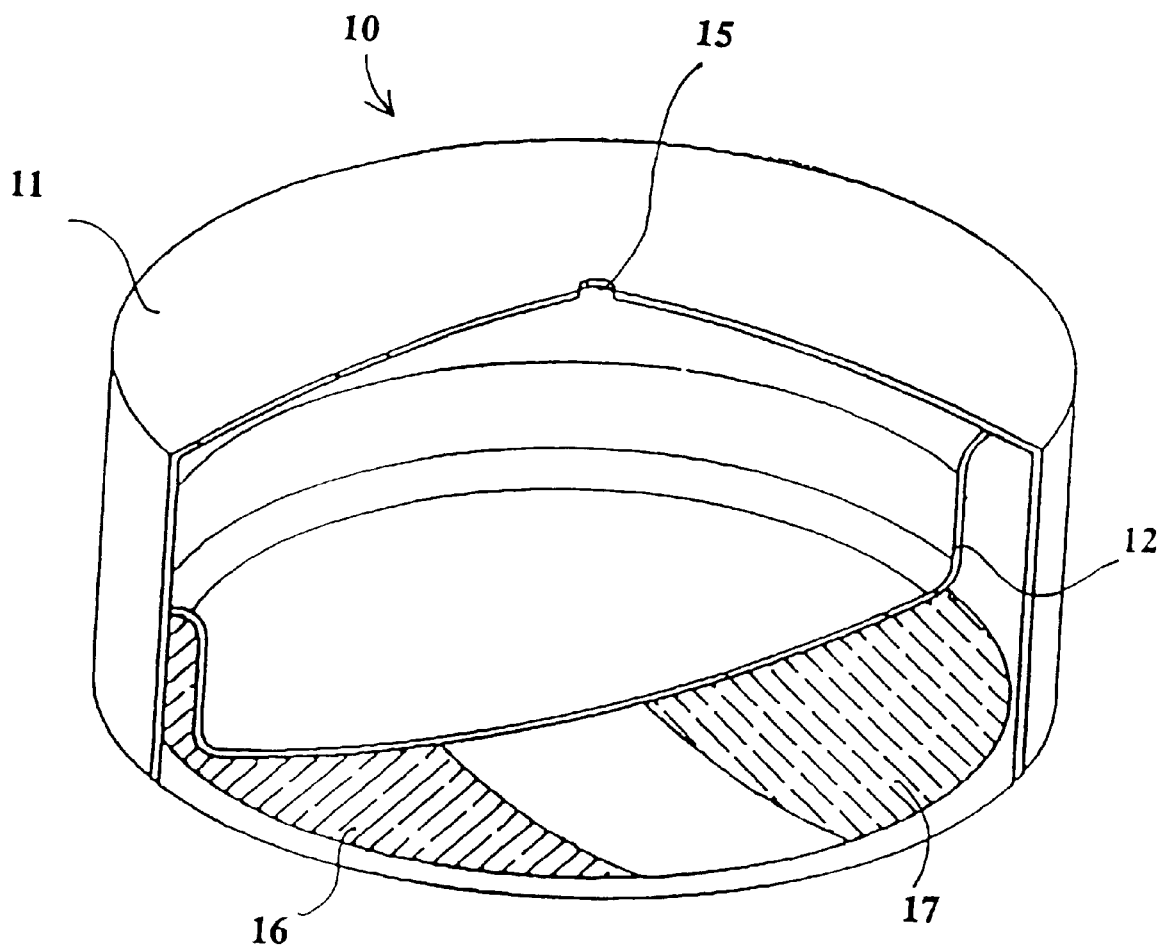
FIG. 3 is a perspective view of a cut away section of the device illustrated in FIG. 2.

In FIG. 3, the device 10 is shown in a perspective view, with part of the housing 11 and the membrane 12 cut away in order to illustrate the structure of the device. Thus, it can be seen that the base of the housing is coated with silver chloride 17 in one region and with nickel 16 in another region. The conductors 18 and printed circuit 19 connecting the silver chloride and nickel electrodes are on the underside of the device 10 as it is viewed in FIG. 3 and accordingly cannot be seen.

We claim:

1. An orally administrable delivery device comprising a housing with walls of a water permeable material and having at least two chambers: a first chamber adapted to receive an active ingredient and which is provided with an orifice through which the active ingredient is expelled under pressure in a liquid form; and a second chamber containing at least one of two spaced-apart electrodes which form part of an electric circuit which is closed by ingress of an aqueous ionic solution into said second chamber, such that a potential difference is set up between the electrodes and a current flows through said circuit resulting in the generation of a gas at said at least one electrode, and the gas once generated acting on a displaceable membrane to compress the first chamber and expel the active ingredient through the orifice for progressive delivery to the gastrointestinal tract.

2. A device according to claim 1, wherein the second chamber contains a pair of spaced-apart electrodes.

3. A device according to claim 2, wherein the electrodes represent an anode and a cathode, the sum of the half-cell reactions of which is positive and wherein at least one of the electrode reactions produces a gas when said electric circuit is closed.

4. A device according to claim 2 or 3, wherein the electrodes are connected by a connection which is isolated from the electrolyte.

5. A device according to claim 4, wherein the connection is external of the second chamber.

6. A device according to any one of claims 1, wherein the electric circuit includes a micro-processor for controlling the generation of gas.

7. A device according to any one of claims 1, wherein the electric circuit includes a sensor for sensing a condition in the body and controls the generation of gas in response to the output of said sensor.

8. A device according to claim 1, wherein the displaceable membrane is flexible.

9. A device according to claim 8, wherein the displaceable membrane is formed of polyvinyl chloride or a silicone rubber.

10. A device according to claim 1, wherein the material of the walls of the device is a non-toxic material which is selected from natural and synthetic materials.

11. A device according to claim 10, wherein the material is a plastics material.

12. A device according to claim 10, wherein the material is made from cellulose or a cellulose derivative.

* * * * *